United States Patent
Liu et al.

(10) Patent No.: US 11,760,980 B2
(45) Date of Patent: Sep. 19, 2023

(54) INDUCED PLURIPOTENT STEM CELLS (IPSCS) AND APPLICATIONS THEREOF

(71) Applicant: CHINA MEDICAL UNIVERSITY, Taichung (TW)

(72) Inventors: Shih-Ping Liu, Taichung (TW); Woei-Cherng Shyu, Taichung (TW); Long-Bin Jeng, Taichung (TW); Chang-Hai Tsai, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 696 days.

(21) Appl. No.: 16/666,286

(22) Filed: Oct. 28, 2019

(65) Prior Publication Data
US 2021/0123026 A1 Apr. 29, 2021

(51) Int. Cl.
| | | |
|---|---|---|
| *A01N 63/00* | (2020.01) | |
| *C07H 21/04* | (2006.01) | |
| *C12N 15/85* | (2006.01) | |
| *C12N 5/074* | (2010.01) | |
| *C12N 15/86* | (2006.01) | |
| *A61P 25/16* | (2006.01) | |
| *A61K 35/545* | (2015.01) | |

(52) U.S. Cl.
CPC ........ *C12N 5/0696* (2013.01); *A61K 35/545* (2013.01); *A61P 25/16* (2018.01); *C12N 15/86* (2013.01); *C07H 21/04* (2013.01); *C12N 2506/1307* (2013.01); *C12N 2510/00* (2013.01); *C12N 2740/15043* (2013.01)

(58) Field of Classification Search
CPC ...... C12N 5/0696; C12N 15/85; C12N 15/86; C12N 2506/00; C12N 2506/1307; C12N 2510/00; C07H 21/04
See application file for complete search history.

(56) References Cited

FOREIGN PATENT DOCUMENTS

WO 2009/006930 A1 1/2009

OTHER PUBLICATIONS

Li et al., 2014, Journal of Hematology & Oncology, 7:50, p. 1-18.*
Sommer et al., 2013, J. Cell. Physiol., vol. 228, p. 267-275.*
Zhang et al., 2012, Cell Cycle, vol. 11, No. 24, p. 1-9.*
Kim et al., 2020, J Biosci, 45:16, p. 1-8.*
Sridharan et al., 2013, Nature Cell Biology, vol. 15, No. 7, p. 872-882.*
Su et al., 2020, Journal of Animal Science, vol. 98, No. 11, p. 1-15.*
Liu, Shih-Ping et al., (2011), "Induced Pluripotent Stem (IPS) Cell Research Overview," Cell Transplantation, vol. 20, pp. 1-100.
Okita, Keisuke et al., (2007), "Generation of germline-competent induced pluripotent stem ceils," Nature, vol. 448, pp. 313-318.
Takahashi, Kazutoshi et al., (2006), "Induction of Pluripotent Stem Cells from Mouse Embryonic and Adult Fibroblast Cultures by Defined Factors," Cell 126, pp. 663-676.
Office Action in Taiwan Counterpart Application No. 108138904, dated Dec. 23, 2020, in 9 pages; English translation provided.
Aloia, Luigi, Bruno Di Stefano, and Luciano Di Croce. "Polycomb complexes in stem cells and embryonic development." Development 140.12 (2013): 2525-2534.
Yu, Junying, et al. "Induced pluripotent stem cell lines derived from human somatic cells." Science 318.5858 (2007): 1917-1920.

* cited by examiner

*Primary Examiner* — Shin Lin Chen
(74) *Attorney, Agent, or Firm* — DUANE MORRIS LLP

(57) ABSTRACT

The present disclosure provides an iPSC cell derived from a somatic cell comprising a Cbx family gene and the applications thereof. Also provided are methods for generating the somatic cells that have potential to become induced pluripotent stem (iPS) cells (iPS cells) without oncogenic properties, and methods for generating iPS cells from the population of cells, which may then be used for transplantation and for cellular differentiation and interaction.

5 Claims, 10 Drawing Sheets
(9 of 10 Drawing Sheet(s) Filed in Color)

INDUCED PLURIPOTENT STEM CELLS (IPSCS) AND APPLICATIONS THEREOF

FIELD OF THE INVENTION

The present disclosure relates to a field of induced pluripotent stem cells (iPSCs). Particularly, the present disclosure provides an iPSC cell derived from a somatic cell comprising a Cbx family gene and the applications thereof.

BACKGROUND OF THE INVENTION

Induced pluripotent stem cells (iPSCs) were firstly generated by Shinya Yamanaka and his colleagues at Kyoto University in Japan in 2006. iPSCs are pluripotent cells, capable of differentiating into all three-germ layers, and therefore possess high potential in clinical application for regeneration medicine.

Yamanaka et al had previously identified 24 factors as the critical factors in embryonic stem cells, which are expressed in embryonic stem cells but not somatic cells (Cell. 2006 Aug. 25; 126(4):663-76). Among the 24 factors, Yamanaka and colleagues further demonstrated that four genes, Oct4, Sox2, c-Myc and KLF4, are essential to reprogram murine fibroblasts into pluripotent cells by introducing 23 of the 24 factors with retroviruses. The four genes, Oct4, Sox2, c-Myc and KLF4, have been thereafter considered conventional reprogramming factors. The pluripotency of cells were then tested for their ability to contribute to embryonic development (i.e. the chimerism in the chimeric mice) (Cell. 2006 Aug. 25; 126(4):663-76).

Two of the four conventional genes, c-Myc and KLF4 are oncogenic, leading to cancer development in 20% of the chimeric mice. However, the efficiency of iPSC generation was very low without c-Myc and KLF4. Therefore, there is a need to develop new genes/factors thereof that are capable of reprogramming somatic cells into iPSs.

SUMMARY OF THE INVENTION

The present disclosure surprising found using a Cbx family gene sequence as reprogramming factor but not cMyc and Klf4 can generate iPSCs which maintains pluripotency and differentiation ability while without oncogenic properties.

In one aspect, the present disclosure provides a population of iPSCs, wherein the genetically modified somatic cells comprise a Cbx family gene sequence and one or more reprogramming factor sequences other than a cMyc family gene sequence and a Klf4 family gene sequence.

In some embodiments, the somatic cell is from ectodermal (e.g., keratinocytes), mesodermal (e.g., fibroblast), endodermal (e.g., pancreatic cells), or neural crest lineage (e.g. melanocytes). In some embodiments, the somatic cell is fibroblast, keratinocyte, pancreatic beta cell, neuron, oligodendrocyte, astrocyte, hepatocyte, hepatic stem cell, cardiomyocyte, skeletal muscle cell, smooth muscle cell, hematopoietic cell, osteoclast, osteoblast, pericyte, vascular endothelial cell or schwann cell. In one embodiment, the somatic cell is fibroblast.

In one embodiment, the Cbx family gene sequence is Cbx7.

In some embodiments, the reprogramming factor sequence includes, but is not limited to, Oct family gene sequence, a Sox family gene sequence, a c-myc family gene sequence, a Klf family gene sequence, a Nanog family gene sequence, a Lin28 family gene sequence and a Glis1 family gene sequence. In further embodiments, the reprogramming factor sequence is Oct family gene sequence, a Sox family gene sequence or a sequence comprising Oct family gene sequence and Sox family gene sequence. Preferably, the Oct family gene sequence is Oct3 or Oct4 and the Sox family gene sequence is Sox2. In further embodiment, the reprogramming factor sequence comprises a sequence of Oct4 and Sox2.

In some embodiments, the somatic cell is from mammal cell. In one embodiment, the mammal cell is a human cell.

In one aspect, the present disclosure provides a pharmaceutical composition comprising a population of iPSCs of the present disclosure, pluripotent stem cells differentiated from the iPSCs of claim 1 or differentiated cells generated from the pluripotent stem cells.

In another aspect, the present disclosure provides a method of generating induced pluripotent stem cells (iPSCs), comprising: (a) introducing somatic cells with a vector expressing a Cbx family gene sequence and one or more vectors expressing one or more reprogramming factor polypeptides rather than a cMyc family polypeptide and a Klf4 family polypeptide; and (b) culturing the resulting somatic cells of (a) under conditions which reprogram the resulting somatic cells of (a) to produce the iPSCs.

In some embodiments, the method further comprises a step of expanding the iPSCs in a stem cell incubation medium in the presence of feeder cells.

In some embodiments, the vector is a lentivirus vector, retroviral vector, adenoviral vector, adenovirus-associated viral vector (AAV), poxvirus vector, herpes virus vector, measles virus vector, foamy virus vector, alphavirus vector, vesicular stomatitis virus vector, transfection vector or transposon vector.

Another aspect of the present invention is a pharmaceutical composition, comprising a population of iPSCs of the present disclosure, pluripotent stem cells differentiated from the iPSCs of the present disclosure or differentiated cells generated from the pluripotent stem cells.

In one aspect, the present disclosure provides a method of generating induced pluripotent stem cells (iPSC), comprising (a) a step of introducing somatic cells with vectors expressing Cbx7 and one or more reprogramming factor sequences other than a cMyc family gene sequence and a Klf4 family gene sequence, and (b) a step of culturing and expanding the iPSC in a stem cell incubation medium in the presence of feeder cells. In one embodiment, the reprogramming factor sequence comprises Oct4 sequence, Sox2 sequence, or a sequence of Oct4 and Sox2. In a further embodiment, the reprogramming factor sequence comprises Oct4 sequence and Sox2 sequence.

Another aspect of the present invention provides a method of treating and/or ameliorating an individual with a disease or disorder in need thereof, comprising administering to the individual an effective amount of cells differentiated from the reprogrammed iPSCs. In one embodiment, the cells differentiated from the reprogrammed iPSCs are pluripotent stem cells.

In one embodiment, the cells differentiated from the reprogrammed iPSCs are neuron stem cells. In one embodiment, the disease or disorder is a neurodegenerative condition. In one embodiment, the neurodegenerative condition is Parkinson's disease, multiple sclerosis (MS), amyotrophic lateral sclerosis (ALS), spinal muscular atrophy (SMA), Huntington's disease, or Alzheimer disease. In a preferred embodiment, the disease or disorder is Parkinson's disease. In one embodiment, the differentiated neuron stem cells are administered at a dose ranging from about $1 \times 10^5$ cells/dose/ day to about 1×10⁸ cells/dose/day. In one embodiment, the differentiated neuron stem cells are administered at a dose of about 1×10⁶ cells/dose/day.

BRIEF DESCRIPTION OF THE DRAWINGS

The patent of application file contains at least one drawing executed in color. Copies of this patent or patent application publication with color drawing(s) will be provided by the office upon request and payment of the necessary fee.

DETAILED DESCRIPTION OF THE INVENTION

Figure 1:
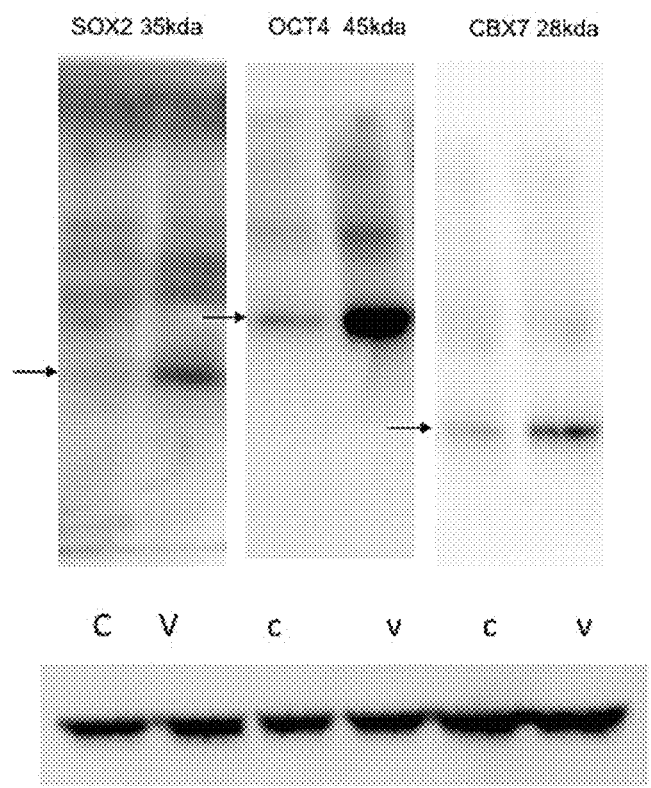
FIGS. 1(A) and (B): The production of lentivirus with 293T cells for the use in transducing mouse embryonic fibroblast (MEF) (A). After the transduction of lentivirus carrying transgenes of Cbx7, Oct4, and Sox2, the protein can be found expressed in the MEF cells (B).
Figure 1:
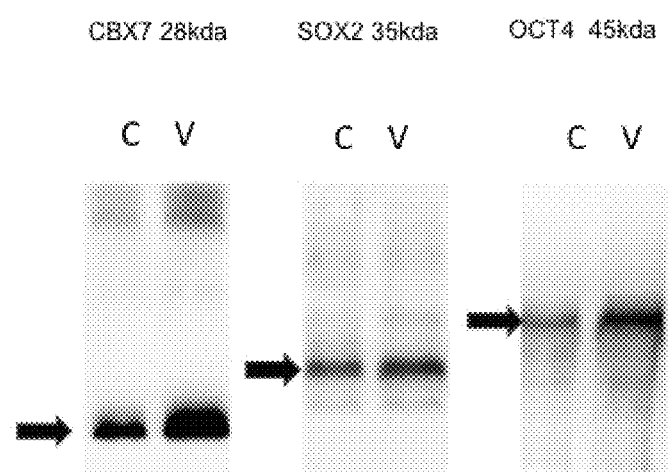

A population of induced pluripotent stem (iPS) cells (iPSCs) derived from genetically modified somatic cells that have an enhanced potential to become without oncogenic properties is provided. Also provided are methods for generating the somatic cells that have potential to become induced pluripotent stem (iPS) cells (iPS cells) without oncogenic properties, and methods for generating iPS cells from the population of cells, which may then be used for transplantation and for cellular differentiation and interaction. These and other objects, advantages, and features of the invention will become apparent to those persons skilled in the art upon reading the details of the subject methods and compositions as more fully described below.

Definition

Unless defined otherwise, all scientific or technical terms used herein have the same meaning as understood by those of ordinary skills in the art to which the present invention belongs. Any method and material similar or equivalent to those described herein can be understood and used by those of ordinary skills in the art to practice the present invention.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the specification and claims of the present invention are approximately that can vary depending upon the desired properties sought to be obtained by the present invention.

The term "a/an" means one or more than one of the objects described in the present invention. The term "and/or" means either one or both of the alternatives. The term "a cell" or "the cell" may include a plurality of cells.

The term "somatic cell" as used herein refers to a cell contributing to the fully-formed body of a multicellular organism outside of the germ line (also referred to as sex cells) and distinguished from the undifferentiated stem cells making up the early embryo.

The terms "reprogram," "reprogrammed," and "reprogramming" as used herein refer to the process by which a differentiated somatic cell is dedifferentiated into a pluripotent stem cell based on ectopic expression of reprogramming factors from transgene vectors, and more broadly to technologically-induced cell lineage conversion in general.

The term "reprogramming factor" as used herein refers to a transgene utilized to promote cellular reprogramming, often (but not necessarily) a transcription factor or microRNA.

The term "in vivo" generally means inside a living organism. The term "ex vivo" generally means outside of a living organism, such as an experiment taking place in an artificial environment created outside of the organism.

The term "three germ layers" refers to the three layers during gastrulation of vertebrates: ectoderm, mesoderm, and endoderm, which derive into all somatic cells.

The terms "pluripotency" and "stemness" of the cell herein refer to the ability of cells, usually stem cells, to give rise to all type of cells in the organism. In the aspect of development biology, a pluripotent cell can give rise to all three germ lineages during embryo development.

The term "embryonic stem cells" refers to the naturally occurring pluripotent cells found in the inner cell mass (ICM) of an embryonic blastocyst. The term "induced pluripotent stem cell" ("iPSC" or "iPS" can be used interchangeably) means the differentiated cells isolated from an adult or fetal organism gaining pluripotency in the artificial process of reprogramming. "iPSCs" is the plurality of iPSC. In contrast to embryonic stem cells, iPSCs are not the pluripotent cells found in nature.

The term "differentiate" or "differentiation" of cells refers to the process of cells losing their pluripotency during cell division, wherein at least one of the daughter cells loses the pluripotency. When cells undergo differentiation, they are in the process of lineage specification to one of the three germ lineages.

The term "introduce" or "transduce" refers to the process of delivering genes into cells through vectors encoding the genes of interest to alter the expression level thereof. Transgenes are the genes or genetic material such as DNA or RNA that are transferred into organisms or cells naturally or by any genetic engineering techniques. Methods in the delivery of transgenes can be via viral vectors or non-viral vectors. In one embodiment of the present disclosure, viral vectors are used to introduce reprogramming factors into cells. The virus vectors can be integrating or non-integrating virus. The integrating virus used in the present disclosure may be lentivirus or retrovirus. The integrating virus allows integration of its encoding genes with the transduced cells that are infected the viral particles. The non-integrating virus used in the present invention may be adenovirus or Sendai virus. Non-viral methods may also be used in this present invention such as by transfecting DNA or RNA materials into cells. The DNA materials can be in the form of PiggyBac, minicircle vectors, or episomal plasmids. The RNA material may be in the form of mRNA or miRNA.

The term "cell culture" or "culture" refers to the process to grow cells under a controlled environment, usually outside of the organism (ex vivo) or outside of its natural environment. The term "dissociate" or "dissociation" in cell culture means to use force or enzymes to disrupt cell aggregates into single cells. The term "trypsinization" refers to the process of using trypsin to digest the extracellular molecules that cells utilize to attach to their growth environment. After trypsinization, cells detach from their growth surface and can be collected with the growth medium. The term "pellet" refers to the cell aggregates resulting from a centrifugal process that allows separating cells from their growth medium. The term "resuspend" or "resuspension" refers to the process of adding new liquid to make cell suspension.

The culture medium in the present invention unless specified is that of conventional laboratory use. The culture medium for feeder cells and MEF cells is DMEM with 10% fetal bovine serum, 1% penicillin and streptomycin, and 1% non-essential amino acids (NEAA). The stem cell incubation medium is DMEM containing 1% L-glutamine, 7.5 ml Hyclone FBS, 0.5 ml NEAA, 91 µl β-mercaptoethanol, and 5 µl leukemia inhibitory factor. A person of ordinary skills in the art will be able to use medium that is similar or equivalent to what is described herein to provide the same or similar growth effect for iPSC.

The term "colony" refers to the aggregate of cells in cell culture that is the result from growth of one single cell. The term "progeny" of cells refers to the daughter cells and the cells derived thereafter cell division/proliferation of the mother cells. The term progeny can be used to define "lineages" of cells, wherein the same lineage of certain cells can be traced through the history of cell division and the progeny of cells.

The term "efficiency of generation" refers the efficiency that from somatic cells reprogramming into the iPS cells. There were many methods to generate the iPS cells from somatic cells, including retrovirus, lentivirus, adenovirus, plasmid transfection, transposon . . . etc. the efficiency to generate iPS cells by each method were different (Cell Transplant. 2011; 20(1):15-9.). (please provide more information:)

The term "embryoid body" or "embryoid bodies" or "EB" refers to the three-dimensional aggregates of pluripotent stem cells in cell culture. Embryonic stem cells or induced pluripotent stem cells within the embryoid bodies undergo differentiation and cell specification along the three germ cell lineages.

The term "feeder cells" or "feeders" refer to cells of one type that are co-cultured with cells of a second type to provide an environment in which the cells of the second type can grow, as the feeder cells provide growth factors and nutrients for the support of the second cell type. The feeder cells are optionally from a different species than the cells they are supporting. The feeder cells may typically be "inactivated" when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, a variety of feeder cells can be used in part to maintain pluripotency, direct differentiation towards a certain lineage and promote maturation to a specialized cell types The term "neural stem cells" refers to the progenitor cells that are capable of giving rise to the neuron and glial cells in the nervous system during the development or regeneration process.

The terms "degenerative disorder" and "degenerative disease" are used interchangeably herein to refer to the result of a continuous process of degenerative cell changes, affecting organ or tissues, and leading to deterioration. The term "neurodegeneration" herein refers to the degenerative disorders resulting from the loss of or dysfunction of central nervous cells. In some embodiments of this invention, neurodegeneration can be artificially induced by introducing agents to disrupt the central nervous system of a subject or an animal model. The term "animal model" refers to an animal with a disease either the same as or like a disease in humans. In some embodiments of the present invention, the disease of the animal model is artificially induced and it is understood by the person skilled in the field of the invention that such model can be translated into the progression of the particular human diseases. The terms "treatment", "treating"

and "treat" generally refer to obtaining a desired pharmacological and/or physiological effect. The effect maybe preventive in terms of completely or partially preventing a disease, disorder, or symptom thereof, and maybe therapeutic in terms of a partial or complete cure for a disease, disorder, and/or symptoms attributed thereto. "Treatment" used herein covers any treatment of a disease in a mammal, preferably a human, and includes (1) suppression of development of disease, disorder, or symptom thereof in a subject or (2) relief from or amelioration of the disease, disorder, or symptom thereof in a subject.

The terms "individual", "subject", and "patient" herein are used interchangeably and refer to any mammalian subject for whom diagnosis, treatment, or therapy is desired.

The term "therapeutically effective amount" refers to the amount of cells or their derived progenies that, when administered to a patient or a subject in need of treatment of a disease or disorder, is sufficient to have a beneficial effect with respect to that disease or disorder. The therapeutically effective amount will vary depending on the conditions of the disease or disorder and its severity. It is not limited to the range stated in the specification. Determining the therapeutically amount of given cells or their derived progeny is within the ordinary skill of the art and requires no more than routine experimentation.

The term "pharmaceutical composition" of this invention includes an effective amount of live cells to treat the degenerative condition. The cell component may be a mixture of culture cells or an isolated population of cells, such as differentiated tissue cells, progenitor cells, and/or stem cells. The pharmaceutical composition of this invention is in liquid form or cell suspension buffer, and may contain pharmaceutical acceptable excipients that stabilize the liquid suspension and help cell viability.

iPSCs of the Present Disclosure and the Production Thereof

It is known in the art that Oct4, Sox2, c-Myc and Klf4 are necessary to generate iPSCs. However, two of the four genes, c-Myc and Klf4, are oncogenic and may cause cancer. The efficiency of generating iPSCs is very low if c-Myc and Klf4 are not used. Cbx7 is downregulated during ESC differentiation and Cbx7 is never used to generate iPS cells generation. The present disclosure surprisingly found that introduction of a Cbx family gene sequence but not c-Myc family gene sequence and Klf4 family gene sequence to somatic cells can efficiently reprogram differentiated cells into iPSCs that do not have oncogenic properties.

Accordingly, the present disclosure provides a population of iPSCs, wherein the genetically modified somatic cells comprise a Cbx family gene sequence and one or more reprogramming factor sequences other than a cMyc family gene sequence and a Klf4 family gene sequence.

Somatic cells are cells that have differentiated sufficiently that they will not naturally generate cells of all three germ layers of the body, i.e. ectoderm, mesoderm and endoderm. They may differentiate to the point that they are capable of giving rise to cells of a specific lineage, e.g. adult non-pluripotent multipotent stem cells, e.g. mesenchymal stem cells, neural stem cells, cardiac stem cells, hepatic stem cells, and the like. Examples of somatic cells include the cells from ectodermal (e.g., keratinocytes), mesodermal (e.g., fibroblast), endodermal (e.g., pancreatic cells), or neural crest lineages (e.g. melanocytes). Certain embodiments include fibroblasts, keratinocytes, pancreatic beta cells, neurons, oligodendrocytes, astrocytes, hepatocytes, hepatic stem cells, cardiomyocytes, skeletal muscle cells, smooth muscle cells, hematopoietic cells, osteoclasts, osteoblasts, pericytes, vascular endothelial cells, schwann cells, and the like. In one non-limiting example, the somatic cell may be a cell of the fibroblast lineage.

Somatic cells are reprogrammed using a Cbx family gene sequence and one or more reprogramming factor sequences (other than a cMyc family gene sequence and a Klf4 family gene sequence). Preferably, the Cbx family gene sequence is a nucleic acid sequence having at least 70% identical to the sequence of Cbx7. More preferably, the Cbx family gene sequence is Cbx7.

The one or more reprogramming factor sequences are preferably Oct family gene sequence, a Sox family gene sequence, a Nanog family gene sequence, a Lin28 family gene sequence. In a preferred embodiment, the one or more reprogramming factor sequences include Oct family gene sequence and a Sox family gene sequence.

Preferably, the Oct family gene sequence is a nucleic acid sequence having at least 70% identical to the amino acid sequence of Oct 3/4. Preferably, the Sox family gene sequence is a nucleic acid sequence having at least 70% identical to the amino acid sequence of Sox2. Preferably, the Nanog family gene sequence is a nucleic acid sequence having at least 70% identical to the amino acid sequence of Nanog. Preferably, the Lin28 family gene sequence is a nucleic acid sequence having at least 70% identical to the amino acid sequence of Lin28.

The iPSC cells of the present disclosure are generated by a method comprising a step of (a) introducing somatic cells with a vector expressing a Cbx family gene and one or more vectors expressing one or more reprogramming factor genes rather than a cMyc family gene and a Klf4 family gene; and (b) culturing the resulting somatic cells of (a) under conditions which reprogram the resulting somatic cells of (a) to produce the iPSCs.

Any appropriate vector expressing the reprogramming factors described herein may be used to introduce transgenes into somatic cells. Suitable vectors notably include plasmid vectors and viral vectors. Viral vectors can be replication-competent or -selective (e.g. engineered to replicate better or selectively in specific host cells), or can be genetically disabled so as to be replication-defective or replication-impaired. Typically, such vectors are commercially available (e.g. in Invitrogen, Stratagene, Amersham Biosciences, Promega, etc.) or available from depository institutions such as the American Type Culture Collection (ATCC, Rockville, Md.) or have been the subject of numerous publications describing their sequence, organization and methods of production, allowing the artisan to apply them.

Representative examples of suitable viral vectors are generated from a variety of different viruses (e.g. retrovirus, adenovirus, adenovirus-associated virus (AAV), poxvirus, herpes virus, measles virus, foamy virus, alphavirus, vesicular stomatitis virus, lentivirus, etc). As described above, the term "viral vector" encompasses vector DNA, genomic DNA as well as viral particles generated therefrom, and especially infectious viral particles. In a preferred embodiment, a retrovirus vector or lentivirus vector. In a preferred embodiment of the present disclosure, a lentivirus is used to introduce transgenes into differentiated cells.

Representative examples of suitable plasmid vectors include, without limitation, pREP4, pCEP4 (Invitrogen), pCI (Promega), pVAX (Invitrogen) and pGWiz (Gene Therapy System Inc.).

Vectors used for providing reprogramming factors to the subject cells as nucleic acids will typically comprise suitable promoters for driving the expression, that is, transcriptional activation, of the reprogramming factor nucleic acids. This may include ubiquitously acting promoters, for example, the CMV-b-actin promoter, or inducible promoters, such as promoters that are active in particular cell populations or that respond to the presence of drugs such as tetracycline.

Subsequently, the genetically modified somatic cells harboring the Cbx family gene sequence and reprogramming factor sequences as described herein can transform to iPSCs by culturing and expanding the resulting somatic cells of under conditions which reprogram the resulting somatic cells to produce the iPSCs in the presence of feeder cells.
Compositions and Applications of the iPSCs of the Present Disclosure The iPSCs are substantially isolated if it is mixed with carriers or diluents, such as culture medium, which will not interfere with its intended use. Alternatively, the iPSC of the invention may be present in a growth matrix or immobilized on a surface.

The iPSCs produced from the above methods may be used for reconstituting or supplementing differentiating or differentiating cells in a recipient through implantation. The induced cells in the recipient may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

The differentiated cells derived from the induced cells may be terminally differentiated cells, or they may be capable of giving rise to cells of a specific lineage. For example, induced cells can be differentiated into a variety of multipotent cell types, e.g., neural stem cells, cardiac stem cells, or hepatic stem cells. The stem cells may then be further differentiated into new cell types, e.g., neural stem cells may be differentiated into neurons; cardiac stem cells may be differentiated into cardiomyocytes; and hepatic stem cells may be differentiated into hepatocytes.

In some embodiments of this invention, the pluripotency of a cell is tested in vivo by examining its capability of growing into teratoma containing all three germ cells. In another embodiment, the pluripotency is tested by the expression of certain markers in cultured cells ex vivo. In yet another embodiment, the pluripotency of a cell is tested by its contribution to the development of an embryo into a living organism. The pluripotent stem cells are injected into the inner cell mass (ICM) of an embryonic blastocyst, which is then implanted into the uterus of a female organism and developing into a fetus. The term "chimerism" refers to the contribution of the stem cells and their progenies to all three germ layers that give rise to various tissues in a living organism.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

In one embodiment, neural stem cells may be generated by culturing the induced cells as floating aggregates in the presence of noggin, or other bone morphogenetic protein antagonist. In another example, neural stem cells may be generated by culturing the induced cells in suspension to form aggregates in the presence of growth factors.

Neural stem cells derived from the induced cells may be differentiated into neurons, oligodendrocytes, or astrocytes. Often, the conditions used to generate neural stem cells can also be used to generate neurons, oligodendrocytes, or astrocytes.

The induced cells, or cells differentiated from the induced cells, may be used as a therapy to treat disease (e.g., a genetic defect). The therapy may be directed at treating the cause of the disease; or alternatively, the therapy may be to treat the effects of the disease or condition. The induced cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from induced cells. The transferred cells also may be multipotent stem cells differentiated from the induced cells. In some cases, the transferred cells may be induced cells that have not been differentiated.

The induced cells may be differentiated into cells and then transferred to subjects suffering from a wide range of diseases or disorders. Subjects suffering from neurological diseases or disorders could especially benefit from stem cell therapies. In some approaches, the induced cells may be differentiated into neural stem cells or neural cells and then transplanted to an injured site to treat a neurological condition, e.g., Alzheimer's disease, Parkinson's disease, multiple sclerosis, cerebral infarction, spinal cord injury, or other central nervous system disorder. Accordingly, another aspect of the present disclosure provides a method for treatment of a neurodegenerative disease using the iPSCs of the present disclosure. In some embodiments, the neurodegenerative disease includes, but is not limited to, Parkinson's disease, multiple sclerosis (MS), amyotrophic lateral sclerosis (ALS), spinal muscular atrophy (SMA), Huntington's disease, or Alzheimer disease. In one embodiment, the iPSC is administered at a dose ranging from about $1 \times 10^5$ cells/dose/day to about $1 \times 10^8$ cells/dose/day. In one embodiment, the differentiated neuron stem cells are administered at a dose of about $1 \times 10^6$ cells/dose/day.

In one embodiment of the present disclosure, iPSCs are differentiated into neural stem cells and/or progenitor cells containing neuron stem cells, which are then administered into the subject in need. A person of ordinary skill in the art will be able to use a method and material similar or equivalent to what is described herein to derive neural stem cells and/or progenitor cell mixture containing neural stem cells from iPSC culture.

In a preferred embodiment, the neuron stem cells differentiated from the iPSCs are administered into subjects in need of treatment of or amelioration from Parkinson's disease. A person of ordinary skill in the art will be able to enrich or isolate the neuron stem cells required for disease treatment and to use a method and material similar or equivalent to what is described herein to for the administration of cells into subjects in need of the desired therapeutic effect.

For the treatment of multiple sclerosis, neural stem cells may be differentiated into oligodendrocytes or progenitors of oligodendrocytes, which are then transferred to a subject suffering from MS.

Diseases other than neurological disorders may also be treated by a stem cell therapy that uses cells differentiated from induced cells, e.g., induced multipotent or pluripotent stem cells. Degenerative heart diseases such as ischemic cardiomyopathy, conduction disease, and congenital defects could benefit from stem cell therapies.

The cells may be introduced to the subject via any of the following routes: parenteral, intravenous, intraarterial, intramuscular, subcutaneous, transdermal, intratracheal, intraperitoneal, or into spinal fluid.

The present invention also provides a pharmaceutical composition, comprising a population of iPSCs of the present disclosure, pluripotent stem cells differentiated from the iPSCs of the present disclosure or differentiated cells generated from the pluripotent stem cells.

According to some embodiments, the composition of the present invention may be formulated with an excipient, carrier or vehicle including, but not limited to, a solvent. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide the desired bulk, consistency, etc., when combined with an active agent and other components of a given composition. Suitable pharmaceutically acceptable carriers for the compositions of the present invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Such carrier solutions also can contain buffers, diluents and other suitable additives. The term "buffer" as used herein refers to a solution or liquid whose chemical makeup neutralizes acids or bases without a significant change in pH. Examples of buffers envisioned by the present invention include, but are not limited to, Dulbecco's phosphate buffered saline (PBS), Ringer's solution, 5% dextrose in water (D5W), normal/physiologic saline (0.9% NaCl). According to some embodiments, the infusion solution is isotonic to subject tissues. According to some embodiments, the infusion solution is hypertonic to subject tissues. Compositions of the present invention that are for parenteral administration can include pharmaceutically acceptable carriers such as sterile aqueous solutions, non-aqueous solutions in common solvents such as alcohols, or solutions in a liquid oil base.

The compositions of the present invention may be administered parenterally in the form of a sterile injectable aqueous or oleaginous suspension. The term "parenteral" or "parenterally" as used herein refers to introduction into the body by way of an injection (i.e., administration by injection), including, but not limited to, infusion techniques. According to some embodiments, parenteral administration includes but is not limited to intravascular delivery (meaning into a blood vessel), intravenous delivery (meaning into a vein), intra-arterial delivery (meaning into an artery), intraosseous delivery (meaning into the bone marrow), intramuscular delivery (meaning into a muscle), subcutaneous delivery (meaning under the skin), cardiac delivery (meaning into the heart, myocardium), etc.

The delivery route may vary and depend on the origin of degenerative diseases. In a preferred embodiment, the delivery route for treating degenerative conditions in central nervous system is intracranial injection.

In one embodiment of the present invention, the cognitive and motor behavior of a subject is examined by the ability of the subject in maintaining its balance in various motions such as running in a rotarod, walking on a beam, or cognitive movement in an open space. The embodiment is not limited to test similar or equivalent to those described herein the present invention. Modifying the methods in testing the cognitive and motor behavior of a subject is within the ordinary skill of the art and requires no more than routine experimentation.

The following Examples illustrate the invention.

EXAMPLE

Example 1 Generation of Induced Pluripotent Stem Cells from Mouse Embryonic Fibroblasts Preparation of Virus Three viral vectors were individually prepared: In one embodiment, lentiviral vector pAS3-Oct4, pAS3-Sox3, and PAS3-Cbx7, was prepared, wherein the cDNA of each gene was commercially available (Thermos Scientific) with the restriction site EcoRI, allowing cloning into pAS3 vectors. The retroviruses or lentiviruses were prepared by using 293T cell line as host cells. Supernatant of transfected 293T cells was collected and concentrated for each retrovirus or lentivirus, which then was used in the preparation of induced pluripotent stem cells (iPSC) (FIG. 1).

Preparation of Mouse Embryonic Fibroblast Cells

Mouse embryonic fibroblast cells (MEF) were used for the preparation of iPSC. Fetuses at E13.5 were extracted from pregnant C57BL6 mice and emerged in a petri dish with phosphate-buffered saline (PBS). Tissues containing MEF were taken by dissecting out limbs, head, tail, and organs from the fetuses, and were minced in the petri dish after being washed three times with PBS. 0.1 mM trypsin/1 mM EDTA solution (GIBCO BRL) was then added to the Petri dish for trypsinization. The minced tissues were then transferred into a conical tube and rocked for 20 minutes on a shaker. Tissue culture medium (DMEM with 10% fetal bovine serum, 1% penicillin and streptomycin, and 1% non-essential amino acids (NEAA)) was subsequently added to the tube. The supernatant was subsequently transferred into a new conical tube and spun in a centrifuge. The cell pellet was resuspended in tissue culture medium and transferred to a petri dish for incubation (5% $CO_2$ and 37° C.).

Feeder cells were used to nurture the fibroblast cell culture and provide growth factors for the later developed iPSCs, preventing the bottom layer of stem cells from differentiation. The feeder cells were derived from MEFs that were incubated with cell culture medium containing Mitomycin C (purchased from Roche) for 2.5 hours at 37° C. Mitomycin C stopped the proliferation of MEFs, which was then subjected to co-culturing with the mouse embryonic fibroblast.

iPSC Cell Culture 6-well plates were coated with gelatin by incubating the plate for 30 minutes in a 37° C. incubator (5% $CO_2$), with 1 ml of 0.2% gelactin in each well. 2 ml of warmed DMEM culture medium was transferred into each well to incubate the freshly-thawed feeder cells overnight at 37° C. with 5% $CO_2$. DMEM medium was replaced with Stem Cell Incubation Medium (42.5 ml of DMEM containing 1% L-glutamine, 7.5 ml Hyclone FBS, 0.5 ml NEAA, 91 μl β-mercaptoethanol, and 5 μl leukemia inhibitory factor), and the cells were subsequently cultured for 1 hour. Induced pluripotent stem cells were then cultured with the feeder cells at 37° C. with 5% $CO_2$. The medium was refreshed two days post cell culture and refreshed everyday afterwards to ensure adequate supply of nutrients to stem cell growth.

Introduction of Cbx-7 to MEF cells (differentiated cells) results in generation of iPSC colonies. Combination of Cbx-7 with Sox-2 and Oct-4 results in an increase of iPSC generation, wherein the efficiency of generation is more than or about 0.01%.

Alkaline Phosphatase Staining

Alkaline phosphatase staining was used to test the stemness of resulting iPSCs or ES cells. After 48 hours of incubation with Stem Cell Incubation Medium, the iPSC or ES cell culture was replaced with various concentrations of fresh N-Butylidenephthalide buffer. After certain length of culture, cells were washed with PBS twice and fixed with 1 ml of 80% ethanol for 2-24 hours at 4° C. Cells were then replaced and immersed in distilled water to wash away the ethanol. An additional wash and immersion for 2-3 minutes with distilled water was applied. After removal of the distilled water, cells were then replaced and immersed in 100 mM Tris-HCl buffer (pH 8.2-8.5) for 5 minutes at room temperature. Tris buffer was removed and replaced with Leukocyte Alkaline Phosphatase Kit for staining for 20-30 minutes. The cells were ready for observation and photography for the activity of alkaline phosphatase after removing the Alkaline Phosphatase Substrate working solution and washed with 100 mM Tris-HCl buffer (pH 8.2-8.5). The activity of alkaline phosphatase was high in stem cells shown red with the substrate staining, while low in differentiated stem cells, shown with weak red or no color activity (FIG. 3).

Immunofluorescence Staining

Figure 3:
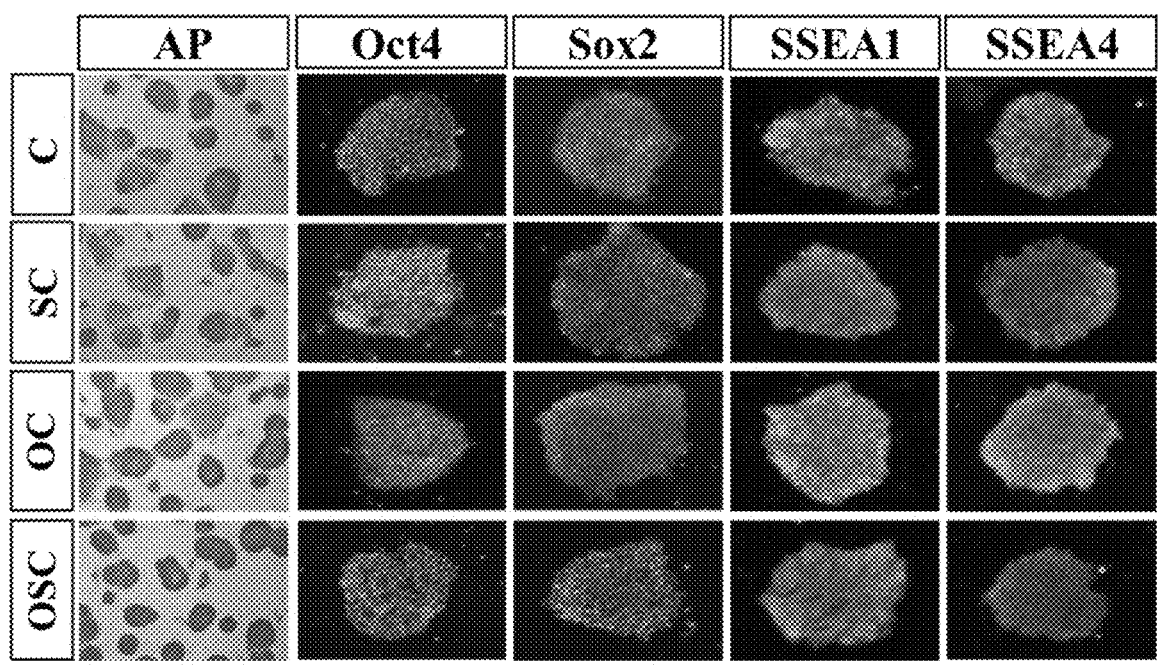
FIG. 3: Immunohistochemistry staining of iPSC cells demonstrate that the reprogrammed iPSC express stem cell markers such as Alkaline phosphatase (AP), Oct4, Sox2, SSEA1, and SSEA4.

Expression of certain markers, such as Nanog, Oct4 and Sox2, can be used to investigate the stemness of stem cell cultures (FIG. 3). To determine the expression of these markers, immunofluorescence staining of these markers was utilized. iPSC or ES cells were subjected to Stem Cell Culture Medium for 48 hours before the staining. Various concentration of fresh N-Butylidenephthalide buffer were used to incubate cells for certain length of time, and cells were washed with PBS and fixed with 4% paraformaldehyde at room temperature for 10 minutes. 0.1% Tween-20/1× PBS was used to wash the cells three times, each time immersed for 10 minutes. Cells were then permeablized by 0.3% Triton-X 100/1× PBS at room temperature for 30 minutes and subjected to blocking with 5% FBS/1× PBS a room temperature for 2 hours. Primary antibodies to the markers of interest were used to stain under 1:100 dilution at room temperature overnight. Cells were then immersed and washed with 0.1% Tween-20/1× PBS for 5 minutes. Fluorescence conjugated-secondary antibodies were used under 1:500 dilution for staining at room temperature for 1 hour. Cells were then immersed and washed with 0.1% Tween-20/1× PBS for 10 minutes. A mounting medium containing DAPI (for DNA staining) was used to mount and seal the cells for observation under inverse microscope.

Introducing MEF cells (differentiated cells) with Cbx7 unexpectedly result in iPSC colony formation. Additionally, introducing the MEF cells with the three factors, Oct-4, Sox-2, and Cbx-7, results in high efficiency of iPSC generation, wherein the reprogrammed iPSC colonies express stem cell markers AP, Oct4, Sox2, SSEA1, and SSEA4 (FIG. 3).

Teratoma Formation

Figure 4:
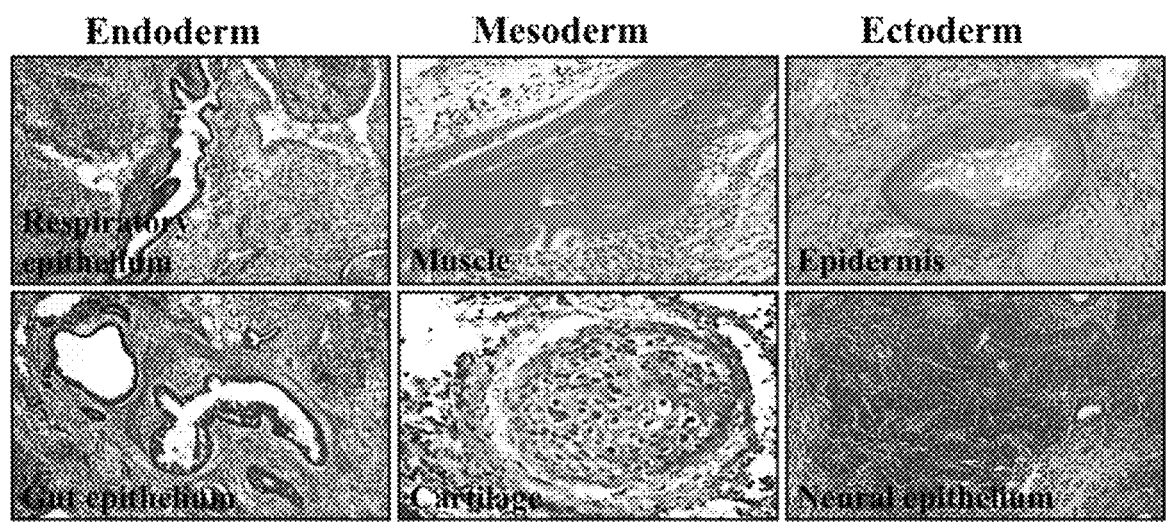
FIG. 4: Teratoma formation in the iPSC-injected nude mice. The presence of all three germ layers, endoderm, mesoderm, and ectoderm, in the iPSC-derived teratoma confirm the pluripotency of iPSC in vivo.

Teratoma formation is a standard method used to investigate the stemness of iPSC or ES cell culture in vivo. To test the stemness of the iPSC culture, iPSCs were injected subcutaneously at the back of SCID mice and teratoma were formed after 6-8 weeks. The tumor/teratoma cells were surgically removed and immersed in 4% paraformaldehyde. Teratoma cells were then frozen and subjected to sectioning of tissues. Tumor slides were then stained with hematoxylin and eosin and observed for the complete development of three germ cell layer: ectoderm, mesoderm, and endoderm (FIG. 4).

Figure 2:
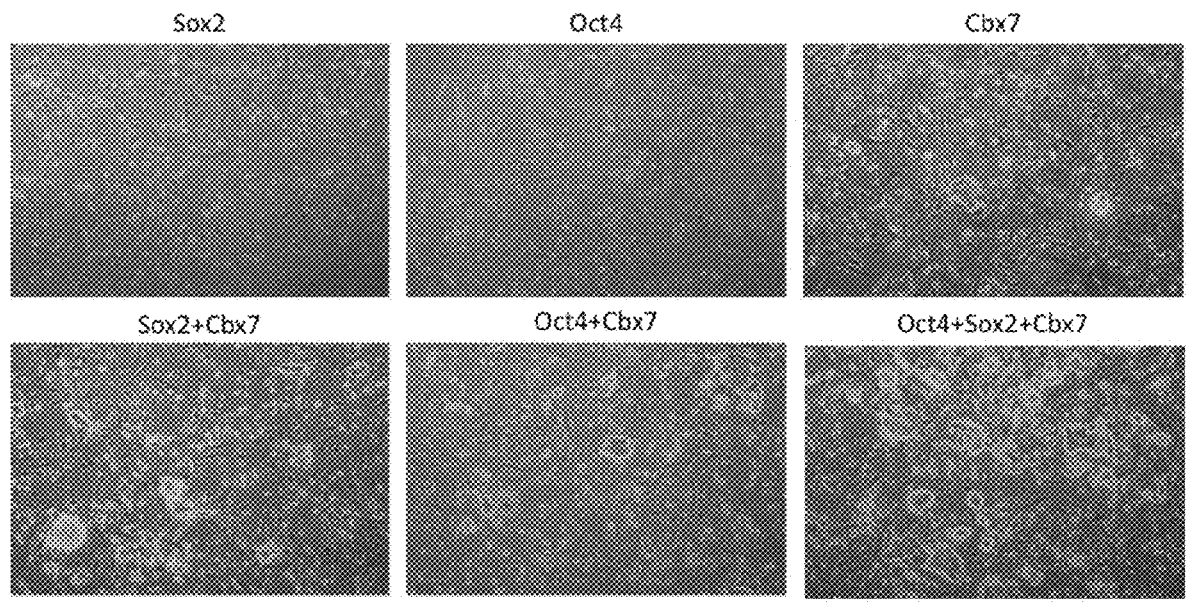
FIGS. 2(A) and (B): The efficiency of iPSC generation with different combination of transgene. The efficiency of iPSC generation is measured by the ability of the transduced-differentiated cells in generating iPSC colonies (A). The bar graph shows the number of colonies generated in this particular experiment (SC: Sox2 and Cbx7; OC: Oct4 and Cbx7; SOC: Sox2, Oct4, and Cbx7) (B).
Figure 2:
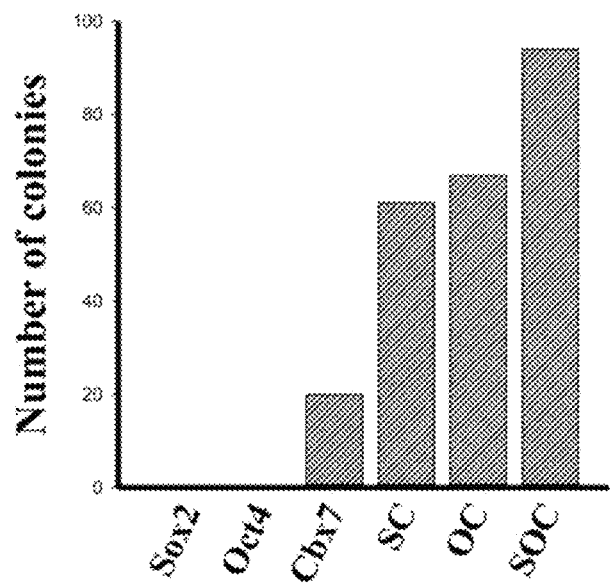

Combination of Cbx7, Oct4, and Sox2 Result in High Efficiency of Generation of iPSC While introducing Sox-2 or Oct-4 generally does not result in iPSC generation, introducing single Cbx-7 gene into differentiated cells results in low efficiency of iPSC generation (FIG. 2). Introducing two genes at once such as Sox2 and Cbx7 or Oct4 and Cbx7 increases the incidence of iPSC generation. The best efficiency of iPSC generation is found in the differentiated cells introduced with three genes: Oct4, Sox2, and Cbx7 (FIG. 2), with which the efficiency of iPSC generation is about 0.01%.

Example 2 Differentiation of iPSC into Neuronal Stem Cells iPSCs were first cultured in Stem Cell Incubation Medium without LIF: 85% DMEM containing 1% L-glutamine, 15% Hyclone FBS, 1% NEAA, 1 mM β-mercaptoethanol, 100 U/ml penicillin, and 100 µg/ml streptomycin. The $2 \times 10^6$ cells in liquid suspension were seeded in each 10 cm$^2$ petri dish, and the cell culture was replaced with fresh Stem Cell Incubation Medium without LIF every other day. Four days after the cells were seeded, iPS derived embryoid bodies (EBs) were transferred to a new petridish, and allowed to seed for 24 hours. The cells were then supplied with ITN-FN culture medium: DMEM/F12 containing 2 mM L-Glutamine, 100 U/ml penicillin, 100 µg/ml streptomycin, 1% ITS-G media supplement, and 5 µg/ml Fibronectin. After 4 days of incubation, cells were then washed twice with PBS, and trypsinized (to detach the cells from petri dish) with 0.05% Trypsin-EDTA for 5 minutes. The detached cells were neutralized with equal volume of Stem Cell Incubation Medium without LIF and transferred to a 15 ml conical tube. The tubes were allowed to stand for 5 minutes to precipitate the larger cell mass (undifferentiated embryoid bodies). Supernatant was transferred to a new conical tube and centrifuged for 5 minutes under 800 rpm. Cell pellet was resuspended and cultured in N-2 medium: DMEM/F12 with 2 mM L-Glutamine, 100 U/ml penicillin, 100 µg/ml streptomycin, 1% N-2 media supplement, and 20 ng/ml bFGF at $1.5 \times 10^5$ cells/ml. Cells were then seeded onto petri dishes pretreated with Poly-L-ornithine/Fibronectin. The Poly-L-ornithine/Fibronectin-pretreated petri dishes were prepared by the following method: incubate petri dish with 15 µg/ml Poly-L-ornithine/PBS solution at 37° C. for 24 hours. Poly-L-ornithine/PBS solution was removed, and the petri dish was washed with PBS buffer for three times and incubated with PBS at 37° C. for 24 hours. PBS was removed from the petridish and washed with freshly prepared PBS. 1 µg/ml Fibronectin/PBS was used to treat petri dish for 6 hours at 37° C. Petri dish was ready for use after the fibronectin solution was removed and the petri dish was washed with PBS.

Figure 5:
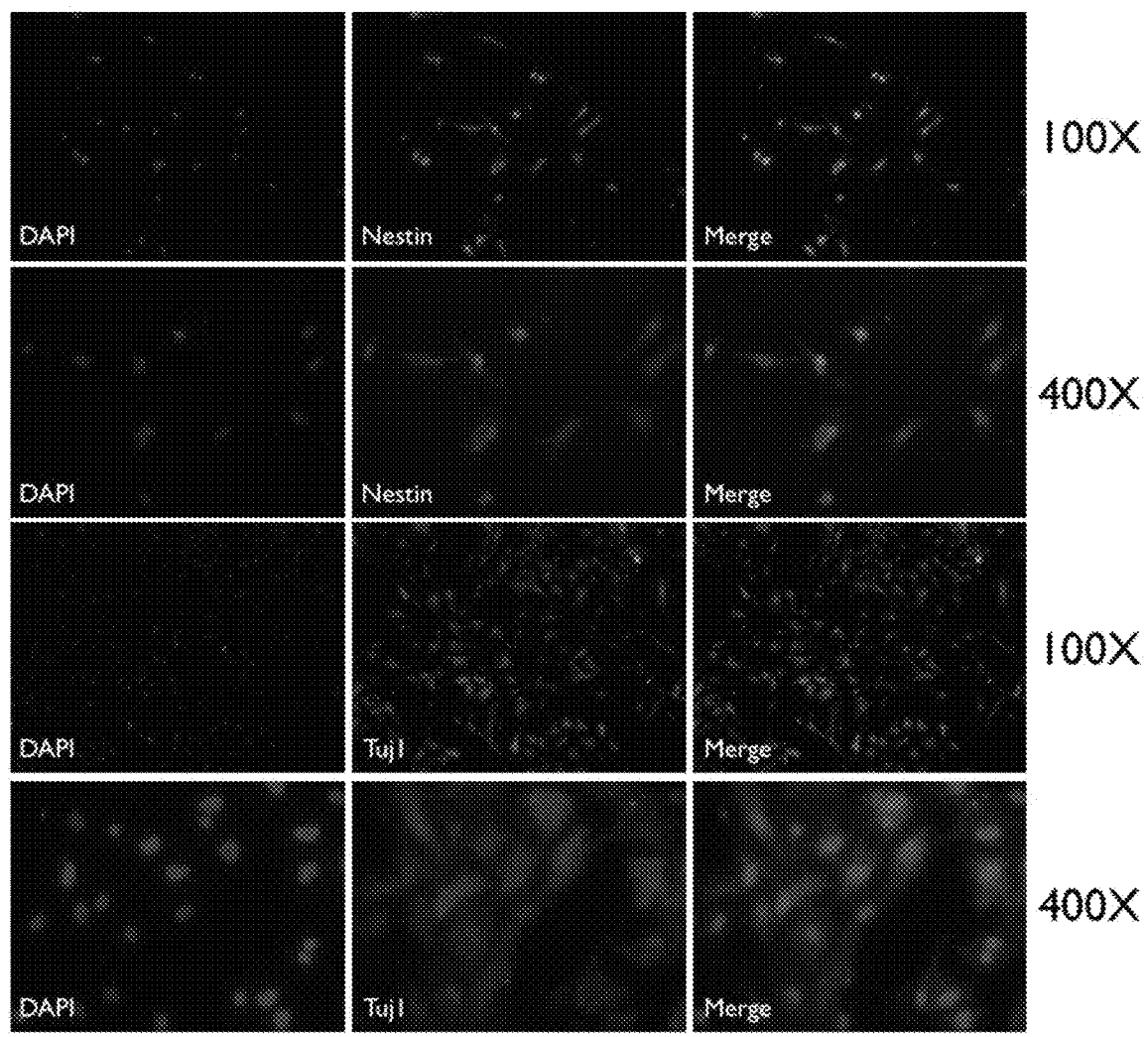
FIG. 5: The reprogrammed iPSCs are capable of giving rise to neuron stem cells, an indication of the differentiation ability of iPSC in vitro.

Cell culture was replenished with 20 ng/ml bFGF daily and with fresh N-2 medium every other day. Cells were passaged to a new petri dish pretreated with Poly-L-ornithine/Fibronectin every 4-5 days and could be passaged up to five times. After differentiation, expression of neuron stem cell makers, Nestin and Tuj1, was determined for iPS-NSCs by immunofluorescent staining (FIG. 5).

Example 3 Use of the iPSC-Differentiated Neuron Stem Cells to Treat Parkinson's Disease An MPTP-Induced Parkinson's Disease Model A working solution of MPTP was prepared in solution at the concentration of 7 mg/ml. Each mouse was given MPTP through intraperitoneal injection at the dose of 20 mg/kg 4 times a day and 2 hours between each dose. It is known by persons skilled in the art that with this dose and procedure, mice develop Parkinson's disease over time.

Transplantation of Neuron Stem Cells

Three points (A, B, and C) were drilled at the right parietal bone and frontal bone for cell transplantation. Point A is located at 0.1 mm to the right of the midpoint between the anterior fontanelle and lambda; point B is located at top of coronal suture; point C is located at the midpoint between point A and point B.

The neuron stem cells were stained with 1 μl/ml of Hoechst 33342 for 1 hours for marking purposes. Afterwards, the neuron stem cells were centrifuged and resuspended in saline. The resuspended cells were sequentially injected into the cranium of mice from point C to A, and then B. The injection depth was 3.5 mm for point A and point C, and 3 mm for point B. A volume of 8 ml of cells were injected with the at each point for the total $1 \times 10^6$ cells/mouse.

Analysis of Animal Behavior

To assess the recovery of animals from Parkinson's disorder, three tools were used to measure and analyze animal behavior: rotarod, locomotor, and beam.

The rotarod measures the capability of an animal to balance and exercise. The rotarod has a rotating axis at the inner side for rodents to climb on and walls to segregate the channels. The size of the rotating axis is 3 cm in diameter and 5 cm in length. The segregating wall is 25 cm in diameter and 1 cm in length. It was previously established that naïve rodent (without any treatment) can stay at the rotating axis for over than 3 minutes at the speed of 5 rpm. The tests were performed every 7 days for a total of 3 times.

Locomotor is an automatic system that allows recording of the activities of animal without any disturbance from outside.

Beam walking is a method to determine the coordination of a rodent on a high and narrow bridge. The size of the beam is 0.6 cm in width and 120 cm in length. There is a dark box (13 cm$^3$) for rodents to rest at one side. The rodent is placed in the dark box for 3 minutes and then placed on beam 15 cm away from the dark box. Once the rodent can walk back to the dark box effortlessly, the distance from the dark box increases to 80 cm. Once the distance of 80 cm is reached, two types of measurement were collected: (1) the length of time for a rodent to walk back from the 80 cm point back to the dark box, and (2) the frequency of a rodent having limb slipped out of the beam. The measurement was collected every 7 days for 3 times.

Figure 6A:
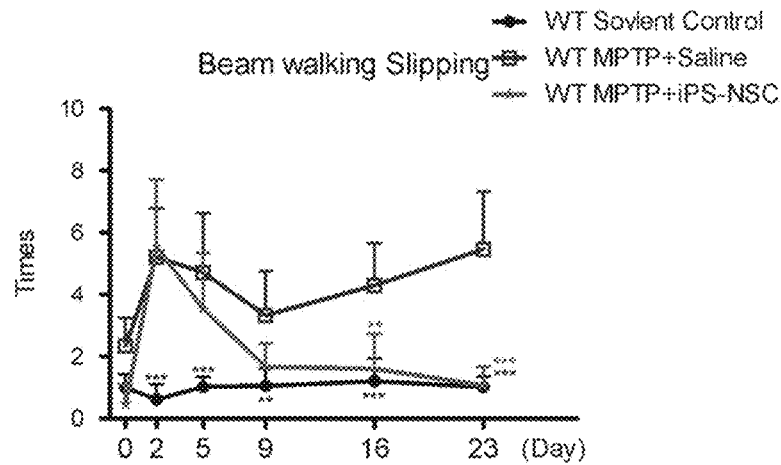
FIGS. 6(A) to (C): In the MPTP-induced Parkinsonian Syndrome model, the differentiated neuron stem cells derived from the reprogrammed iPSC (iPS-NSC) significantly improve animal behavior in beam walking and rotarod movement (*p<0.05. **p<0.01). (A and B) Bean walking behavior analysis was used to test the balance ability of mice. Transplantation with iPS-derived neuron stem cells (iPS-NSC) significantly improved balancing ability (including slipping (A) and time of passage (B)) compared to that in mice transplanted with Saline. (C) iPS-NSC treated mice improved coordination ability compared to that in mice transplanted with Saline by Rotarod analysis.
Figure 6B:
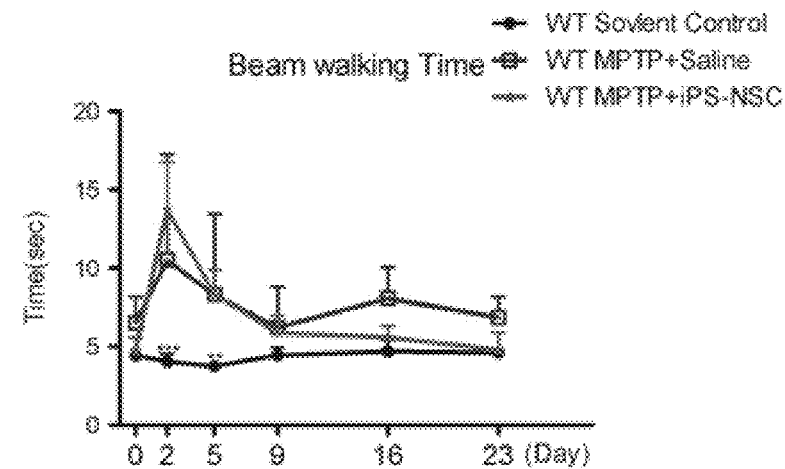
Figure 6C:
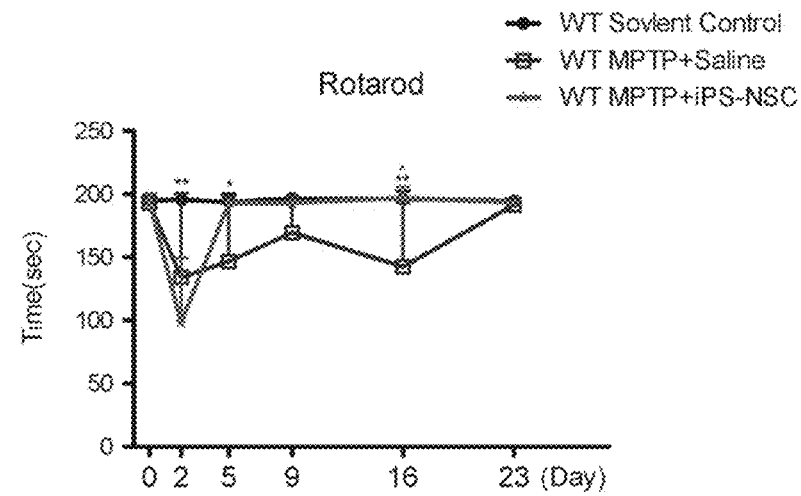
Figure 7A:
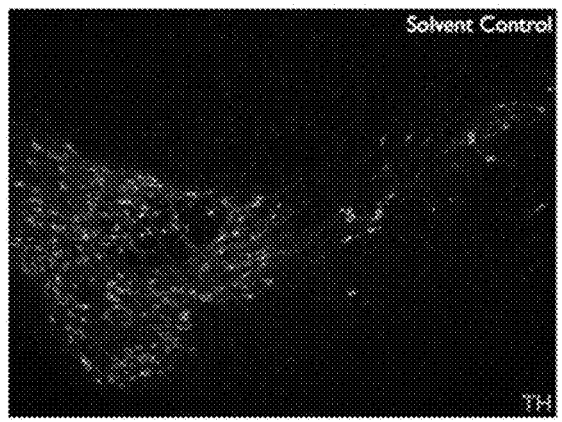
FIGS. 7(A) to (D): Number of tyrosine hydroxylase (TH)-expressing cells in mice: (A) solvent control; (B) MPTP treatment to induced Parkinson disease; (C) MPTP treatment to induced Parkinson disease and transplanted with iPS-NSC. (D) Cells positive for TH were counted and presented as percentage versus MPTP group in the bar graph. Error bars represent means+SDs. Increased number of dopamine secreting neurons in the substantia nigra after iPS-NSC treatment. The dopamine secreting neurons (TH positive cells) are found decreased in the MPTP-injured group, wherein the treatment of iPS-NSC rescue the number of TH positive cells.
Figure 7B:
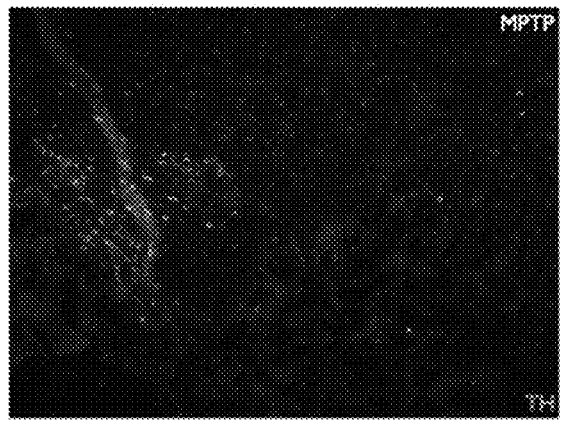
Figure 7C:
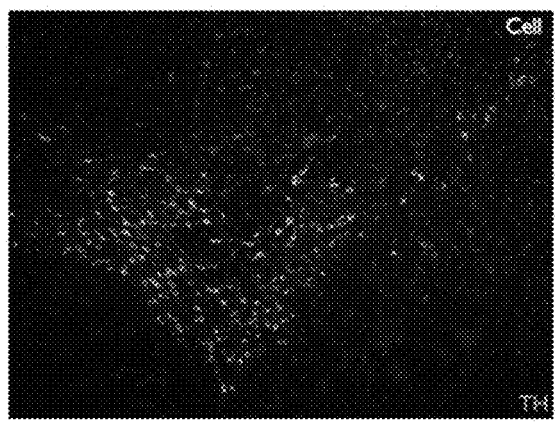
Figure 7D:
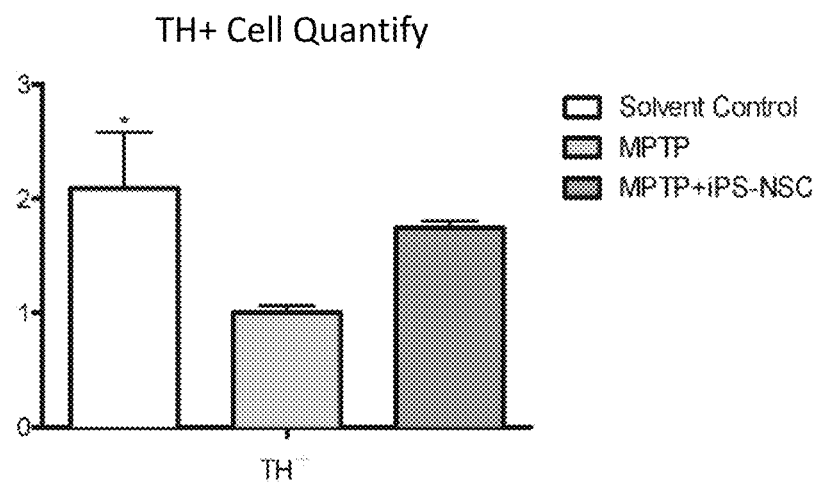
Figure 8A:
FIGS. 8(A) to (D): Number of Iba1-expressing cells in mice: (A) solvent control; (B) MPTP treatment to induced Parkinson disease; (C) MPTP treatment to induced Parkinson disease and transplanted with iPS-NSC. (D) Cells positive for Iba1 were counted and presented as percentage versus MPTP group in the bar graph. Error bars represent means+SDs. Decreased immune response in striatum after iPS-NSC treatment. Iba1 positive cells are found increased in the MPTP-injured group, wherein the treatment of iPS-NSC significantly reduces the Iba1 positive cells, indicating a decrease immune response. (***p<0.001)
Figure 8B:
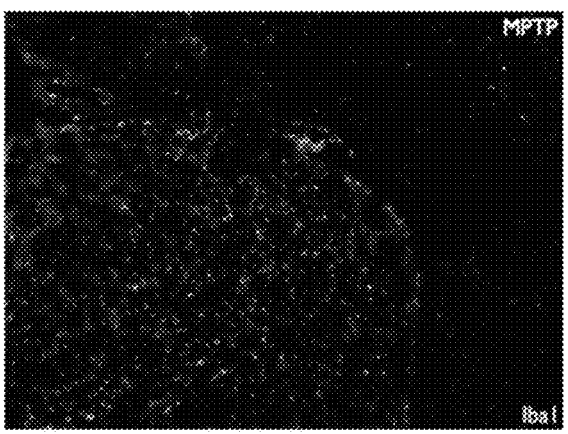
Figure 8C:
Figure 8D:
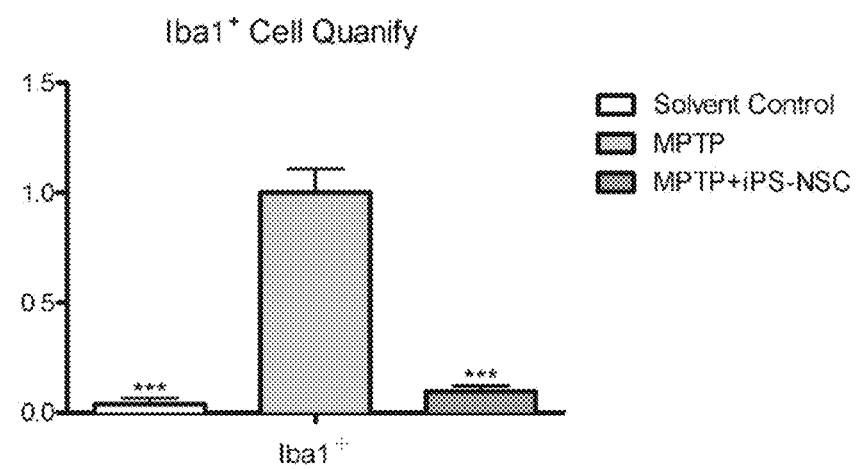

In the MPTP-induced Parkinsonian Syndrome model, the differentiated neuron stem cells derived from the reprogrammed iPSC (iPS-NSC) significantly improve animal behavior in beam walking and rotarod movement (*$p<0.05$. $p<0.01$). Bean walking behavior analysis was used to test the balance ability of mice. Transplantation with iPS-derived neuron stem cells (iPS-NSC) significantly improved balancing ability (including slipping (FIG. 6A) and time of passage (FIG. 6B)) compared to that in mice transplanted with Saline. In addition, Rotarod analysis was used to test the coordination ability of mice. iPS-NSC treated mice improved coordination ability compared to that in mice transplanted with Saline group (FIG. 6**C).

The iPSC-Differentiated Neuronal Stem Cells are Capable of Treating Parkinson's Disorder We also obtained the TH positive cells (dopamine neuron) numbers in substantia nigra by immunofluorescence staining. The results show an increase number of TH positive cells in iPS-NSC treated group when compared to the saline treated group. This data indicate that the treatment of iPSC-derived neuron stem cell (iPS-NSC) treatment rescues the number of dopamine neurons in substantia nigra (FIG. 7). In addition, a significantly decreased number of Iba1 positive cells, immune cells as indication of inflammation, is found in the iPS-NSC treated group, indicating a decreased immune response. in the MPTP-induced Parkinson's disease model (FIG. 8).

Level of Serum Dopamine is Increased by the iPS-NSC Treatment in the MPTP-Induced Parkinson's Disease Analysis for dopamine level with a ELISA kit-500 μl of blood were collected from the mice a day prior to the behavior assessment with retro-orbital bleeding. The collected blood was allowed to stand at room temperature for 30 minutes and spun at the speed of 1,000 rpm at 4° C. for 10 minutes. Serum/supernatant was collected and stored at −20° C. for subsequent analysis. The ELISA experiments were performed with the Enzyme-Immunosorbent Assay Kit for Dopamine purchased from Uson.

Figure 9:
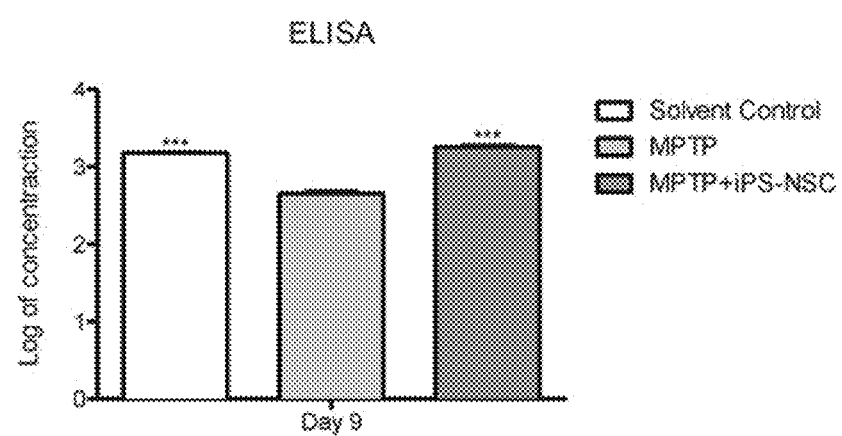
FIG. 9: Level of serum dopamine is increased with the iPS-NSC treatment in the MPTP-induced Parkinson's disease model (***p<0.001).
Figure 10A:
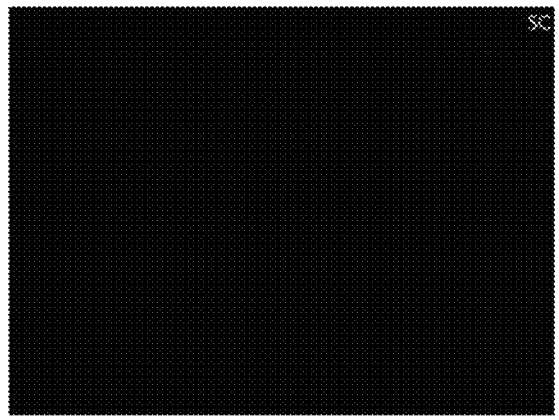
FIGS. 10(A) to (D): Number of apoptosis cells in mice by TUNEL assay: (A) solvent control; (B) MPTP treatment to induced Parkinson disease; (C) MPTP treatment to induced Parkinson disease and transplanted with iPS-NSC. (D) Cells positive for TUNEL assay were counted and presented as percentage versus MPTP group in the bar graph. Error bars represent means+SDs. Decreased neuron cell death in the substantia nigra after iPS-NSC treatment. iPS-NSC treatment significantly decreases cell death when compared to the MPTP-injured control group (**p<0.01).
Figure 10B:
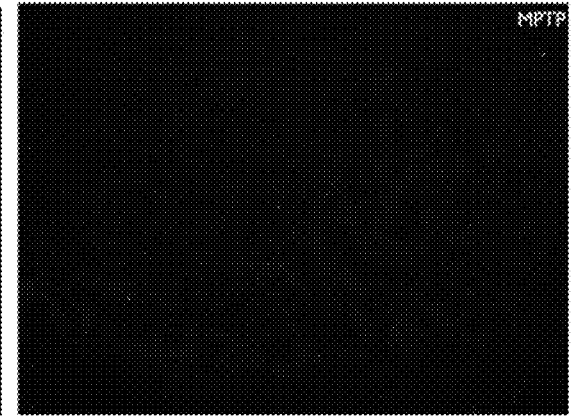
Figure 10C:
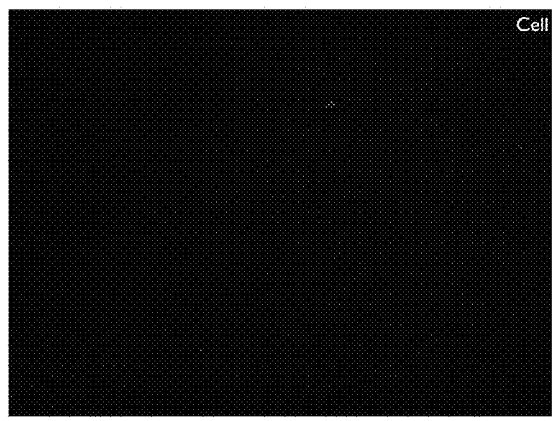
Figure 10D:
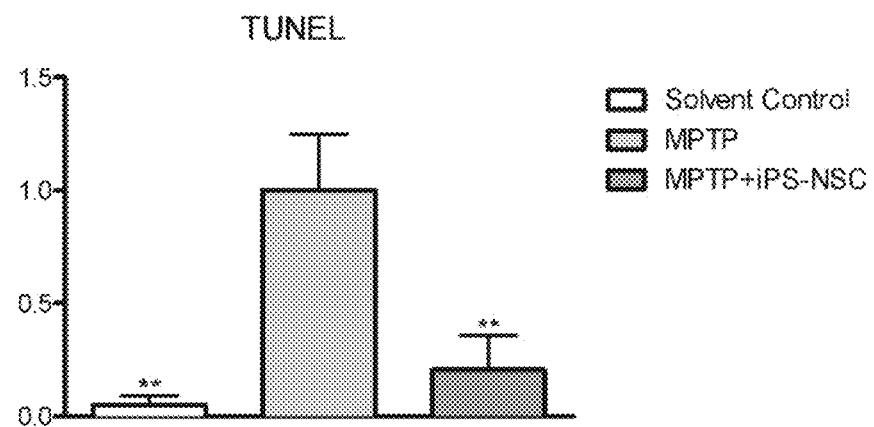

The level of dopamine was measured in the MPTP-induced Parkinson's disease model. It is found that iPS-NSC rescue the dopamine level in serum to a comparable level with the uninjured control, indicating a capability of neuron repair by the iPS-NSC cells (FIG. 9).

Immunofluorescence Staining and Analysis

After behavior assessment, mice were sacrificed and dissected for the collection of the brain tissue. The brain tissue was fixed with 4% paraformaldehyde and frozen with OCT. Brain sections were placed on the slides and washed with TBST/PBST for 5 minutes to clean the remaining OCT from the border of brain tissues. Antigen retrieving was performed by immersing the slides in antigen retrieving solution (12.5 ml Trilogy in 237.5 ml of ddH$_2$O) and steaming them for 3 minutes in a cooker. The slides were then washed with TBST/PBST for 10 minutes. Tissue cells were permeablized by incubating them with 0.3% Triton-X100 for 30 minutes at room temperature and washed with TBST/PBST for 10 minutes. The slides were then blocked with blocking buffer containing 5% FBS for 1 hour at room temperature. The primary antibodies against a marker of interest were added to the block buffer and incubated at 4° C. overnight. Slides were washed with TBST/PBST for 10 minutes and incubated with secondary antibodies for 1 hour at room temperature. After being washed with TBST/PBST for 10 minutes, slides were stained with PI for 15 minutes at room temperature. Slides were then washed once again with TBST/PBST for 10 minutes and sealed with mounting medium.

TUNEL Assay of the MPTP-Induced Parkinson's Disease Model

To measure the cell death within the brain tissue collected from the mice, TUNEL assay was performed with the brain section on the slides. The experiments were performed using a commercially available kit "DeadEnd™ Fluorometric TUNEL System". A person of ordinary skill in the art will be able to understand and perform this experiment by reagents similar to or equivalent to what is described herein.

Slides were washed with PBS for 5 minutes, and then transferred to 0.2% Triton-100/PBS for a 5-minute incubation to permeabilize the cell membranes. Afterwards, the slides were washed twice, 5 minutes each time. The slides then were incubated at room temperature for 10 minutes in a dark staining box with 100 µl of Equilibration Buffer, and 50 µl of TdT Mix was added to each sample. The slides were further incubated in the dark at 37° C. for 1 hour. Afterwards, the reaction was stopped by incubating the slides with 2×SSC buffer for 15 minutes. The slides were washed three times by incubating them with PBS for 5 minutes each, stained with DAPI, and then sealed with mounting medium.

As a result, it is found that the iPS-NSC treated mice present a significantly low level of cell death in substantia nigra when compared to the MPTP-injured control group. The level of cell death is comparable to the uninjured solvent control group, indicating the rescue capability of iPS-NSC cells in the neuron regeneration (FIG. 10).

What is claimed is:

1. A population of induced pluripotent stem cells (iPSCs) derived from genetically modified somatic cells, wherein the genetically modified somatic cells comprise a vector expressing Chromobox (Cbx)7 gene sequence and one or more reprogramming factor sequences selected from an Oct family gene sequence and a Sox family gene sequence,
wherein the somatic cells comprise human fibroblasts.

2. The population of iPSCs of claim 1, wherein the reprogramming factor sequence comprises the Oct family gene sequence and the Sox family gene sequence.

3. The population of iPSCs of claim 2, wherein the Oct family gene sequence is Oct3 or Oct4 and the Sox family gene sequence is Sox2.

4. The population of iPSCs of claim 1, wherein the reprogramming factor sequence comprises Oct4 and Sox2.

5. A pharmaceutical composition, comprising the population of iPSCs of claim 1, multipotent stem cells differentiated from the population of iPSCs of claim 1 or terminally differentiated cells generated from the multipotent stem cells.

* * * * *